(12) United States Patent
Takahashi et al.

(10) Patent No.: US 9,855,195 B2
(45) Date of Patent: Jan. 2, 2018

(54) DENTAL CURABLE COMPOSITION

(71) Applicants: KABUSHIKI KAISHA SHOFU, Kyoto-shi, Kyoto (JP); JGC CATALYSTS AND CHEMICALS LTD., Kawasaki-shi, Kanagawa (JP)

(72) Inventors: Shuhei Takahashi, Kyoto (JP); Hidefumi Fujimura, Kyoto (JP); Jun Uchida, Kyoto (JP); Mitsuji Teramae, Kyoto (JP); Kunio Hori, Kitakyushu (JP); Naoyuki Enomoto, Kitakyushu (JP)

(73) Assignees: KABUSHIKI KAISHA SHOFU, Kyoto (JP); JGC CATALYSTS AND CHEMICALS LTD., Kanagawa (JP)

( * ) Notice: Subject to any disclaimer, the term of this patent is extended or adjusted under 35 U.S.C. 154(b) by 0 days.

(21) Appl. No.: 15/267,345

(22) Filed: Sep. 16, 2016

(65) Prior Publication Data
US 2017/0079890 A1    Mar. 23, 2017

(30) Foreign Application Priority Data
Sep. 17, 2015  (JP) .................................. 2015-184168

(51) Int. Cl.
| | | |
|---|---|---|
| *A61K 6/00* | (2006.01) | |
| *A61K 6/027* | (2006.01) | |
| *A61K 6/02* | (2006.01) | |
| *A61K 6/083* | (2006.01) | |

(52) U.S. Cl.
CPC .......... *A61K 6/0097* (2013.01); *A61K 6/0008* (2013.01); *A61K 6/0073* (2013.01); *A61K 6/0088* (2013.01); *A61K 6/024* (2013.01); *A61K 6/027* (2013.01); *A61K 6/0235* (2013.01); *A61K 6/0255* (2013.01); *A61K 6/083* (2013.01)

(58) Field of Classification Search
None
See application file for complete search history.

(56) References Cited

U.S. PATENT DOCUMENTS

| | | | | |
|---|---|---|---|---|
| 2002/0022677 A1* | 2/2002 | Teramae | ............... | A61K 6/0023 523/113 |
| 2003/0089276 A1* | 5/2003 | Nishida | ............. | C04B 35/62655 106/35 |
| 2006/0058414 A1* | 3/2006 | Arthur | ................. | A61K 6/0017 523/116 |
| 2006/0058415 A1* | 3/2006 | Arthur | ................. | A61K 6/0017 523/116 |
| 2006/0058416 A1* | 3/2006 | Brandenburg | ....... | A61K 6/0017 523/116 |
| 2006/0058417 A1* | 3/2006 | Brandenburg | ....... | A61K 6/0017 523/116 |
| 2006/0058418 A1* | 3/2006 | Brandenburg | ....... | A61K 6/0017 523/116 |
| 2007/0292623 A1* | 12/2007 | Lin | .......................... | C09D 1/00 427/407.1 |
| 2008/0021147 A1* | 1/2008 | Lin | ........................ | B82Y 30/00 524/493 |
| 2008/0160289 A1* | 7/2008 | Lin | ........................ | B82Y 30/00 428/327 |
| 2017/0079890 A1* | 3/2017 | Takahashi | ............. | A61K 6/0073 |

FOREIGN PATENT DOCUMENTS

| | | | | |
|---|---|---|---|---|
| JP | 7-196428 | 8/1995 | | |
| JP | 2002037619 A | * 2/2002 | ............. | C01B 33/18 |
| JP | 3481660 | 12/2003 | | |
| JP | 4034958 | 1/2008 | | |
| JP | 4042313 | 2/2008 | | |

OTHER PUBLICATIONS

Extended European Search Report dated Dec. 23, 2016 in corresponding European patent application No. 16189166.8.
Database WPI, Week 199539, Thomson Scientific, London, GB; AN 1995-299449, XP002765194.

\* cited by examiner

*Primary Examiner* — Peter A Salamon
(74) *Attorney, Agent, or Firm* — Wenderoth, Lind & Ponack, L.L.P.

(57) ABSTRACT

The present invention provides a dental curable composition used for dental filling restorative materials, dental crown prosthesis materials such as inlays, crowns, and bridges, materials for constructing anchor teeth, block materials for dental CAD/CAM, etc. More specifically, the present invention provides a dental curable composition comprising a curable resin (A), a porous inorganic filler (B), and a polymerization initiator (C), wherein the porous inorganic filler (B) comprises a silicon dioxide, and an oxide comprising at least one kind of the other metallic elements, and a ratio ($I_1/I_2$) of a maximum absorbance ($I_1$) of 3730 to 3750 $cm^{-1}$ to a maximum absorbance ($I_2$) of 3000 to 3600 $cm^{-1}$ in infrared absorption spectrum of the porous inorganic filler (B), is not less than 1 and not more than 3.

2 Claims, No Drawings

DENTAL CURABLE COMPOSITION

TECHNICAL FIELD

The present invention relates to a dental curable composition used in dental filling restorative materials, dental crown prosthesis materials such as inlays, crowns, and bridges, materials for constructing anchor teeth, block materials for dental CAD/CAM, etc.

BACKGROUND ART

In recent years, dental curable compositions comprising curable resins and inorganic fillers have been widely used. These are generally called dental composite resins and utilized for various uses such as direct restorative materials for tooth defective parts due to dental caries, etc., dental crown prosthesis restorative materials such as inlays, crowns, and bridges, materials for constructing anchor tooth for dental crown defective parts, block materials for dental CAD/CAM, etc. These dental curable compositions are preferable which have a higher mechanical strength, color tone compatibility with natural teeth, and a transparency equivalent to natural teeth, and further durability on aged deterioration of mechanical strength, etc, is preferable under severer oral circumstances.

The various properties which such a dental curable composition needs, are greatly affected by compositions, particle sizes, shape, etc. of the inorganic filler. The technological background of the inorganic filler which has been used in the dental curable compositions is shown below.

The initial inorganic filler used in the dental curable compositions was a macro-filler having a mean particle size of approximately 5-30 µm obtained by pulverizing massive quartz, silicate glass, etc. Although the dental curable composition containing such a macro-filler was excellent in mechanical strength such as bending strength, the composition has had a poor polishing property, and a defect that the inorganic filler is decreased off due to its abrasion. The submicro filler pulverized to a mean particle size of approximately 0.5-3 µm is used by proceed of trituration technology. However, in the dental curable composition using the submicro filler, realization of its enough high mechanical strength has not been accomplished.

On one hand, a micro filler comprising ultrafine particles having a mean particle size of approximately 0.01-0.05 µm as primary particles, a representative of which is colloidal silicon dioxide obtainable by a combustion hydrolysis method of organosilane compounds, is also used. Although a dental curable composition obtainable by combining the micro filler is excellent in the surface glossiness after polishing, the viscosity of the dental curable composition increases when the micro filler is filled up. When the viscosity of the dental curable composition increases, its filler filling ratio has to be decreased and thereby a higher mechanical strength could not be conferred to the dental curable composition. Moreover, combination of the micro filler also has the defect that the dental curable composition becomes pale opaque according to the scattering phenomenon (Rayleigh scattering) of the light originated from ultrafine particles.

In recent years, research and development on inorganic fillers are proceeded and new types of fillers as described below have been developed. In Patent Document 1, an inorganic filler is proposed which forms independent amorphous layers of a silicon dioxide and at least one kind of the other metal oxides, wherein the silicon dioxide is produced by aggregating a silicon dioxide and at least one kind of the other metal oxides and heat-treating them at a temperature of less than crystallization of the metal oxides. The above-mentioned invention provides a dental composite material which is excellent in lubricating property of a polished surface of the cured material, or color tone compatibility with natural teeth, and which has an opacity over X-rays. However, the inorganic filler of the above-mentioned invention has an insufficient adjustment of pore volume of particles or particle strength, and the dental curable composition which uses the inorganic filler did not have a sufficient mechanical strength.

Patent Document 2 proposes an inorganic filler comprising silicon dioxide and an inorganic oxide other than the silicon dioxide, wherein 5 to 70% by weight of the silicon dioxide is originated from an acidic silicic acid solution, and 30 to 95% by weight of the silicon dioxide is originated from a silica sol. Since the inorganic filler of the above-mentioned invention is amorphous and has X-ray contrast property and the refractive index, pore volume, particle strength, etc. of its particles are adjustable, a porous inorganic filler having pores physically fittable to curable resins can be provided. As a result, since mechanical strength of the dental curable composition comprising the above-mentioned porous inorganic filler is enhanced and the refractive index of its particles can be freely controlled, an excellent transparency equivalent to that of natural teeth can be conferred to the dental curable composition without selecting the kind of the curable resins. However, in Patent Document 2, there were problems that a mechanical strength sufficient as that of a dental curable composition has not been still accomplished, or its durability on aged deterioration was low.

The inorganic filler is silanized by using silane coupling materials in order to improve adaptation to a curable resin. The silane coupling materials have a functional group which forms a chemical bonding with a silanol group of the inorganic filler, and a functional group which forms a chemical bonding with the curable resin. The inorganic filler processed by the silane coupling materials has a good adaptation to the curable resin to increase the filling rate of the dental curable composition to contribute to an improvement in its mechanical strength. In the porous inorganic filler of Patent Document 2, although a physical fitting with the curable resin is obtained, the silanol group for forming a chemical bonding with the silane coupling materials is poor in numbers. Therefore, a sufficient chemical bonding was not obtained between the filler and the coupling materials. As a result, a sufficient mechanical strength for the dental curable composition is not revealed, and it was considered that unreacted coupling materials, or the silanol group, etc. deteriorate by water absorption, and that the durability on aged deterioration of the dental curable composition was low.

Patent Document 3 provides a method for conferring an active isolated silanol group to an inorganic filler which mainly comprises an inactive silicon dioxide. There is exhibited that the inorganic filler enhances chemical bonding with silane coupling materials, and confers an excellent mechanical strength or moisture resistance to its cured body. However, the above-mentioned inorganic filler did not comply with properties such as mechanical strength, and a transparency equivalent to that of natural teeth, which are required of the dental curable composition. Therefore, a dental curable composition has been desired which has a transparency equivalent to that of natural teeth which the conventional dental curable composition has, and has a further improvement of mechanical strength and a durability on aged deterioration.

REFERENCE DOCUMENTS

Patent Documents

Patent Document 1: Japanese Patent No. 3481660 B
Patent Document 2: Japanese Patent No. 4034958 B
Patent Document 3: Japanese Patent No. 4042313 B

SUMMARY OF THE INVENTION

Problems to be Solved by the Invention

The object of the present invention is to provide a dental curable composition which is used in dental crown prosthesis materials such as inlays, crowns, and bridges, materials for constructing anchor tooth, block materials for dental CAD/CAM, etc., and which has an improvement of a mechanical strength or a durability on aged deterioration while having a transparency equivalent to that of natural teeth which the conventional dental curable composition has.

Means for Solving the Problems

The present inventors intensively studied the above-mentioned problems to accomplish them. As a result of the study, the inventors overcame those problems by providing a dental curable composition comprising a curable resin (A), a porous inorganic filler (B), and a polymerization initiator (C), wherein the porous inorganic filler (B) comprises a silicon dioxide and an oxide comprising at least one kind of the other metallic elements, and a ratio $(I_1/I_2)$ of a maximum absorbance $(I_1)$ at 3730 to 3750 $cm^{-1}$ to a maximum absorbance $(I_2)$ at 3000 to 3600 $cm^{-1}$ in the infrared absorption spectrum of the porous inorganic filler (B), is not less than 1 and not more than 3. The present invention is based on the above-mentioned knowledge. Moreover, at least one kind of the other metallic elements of the above-mentioned porous inorganic filler (B) is preferably an oxide which at least contains a zirconium element.

Effects of the Invention

The present invention can provide the dental curable composition having an excellent mechanical strength and a durability on aged deterioration while having a transparency equivalent to that of natural teeth.

MODES FOR CARRYING OUT THE INVENTION

The details of the present invention are explained below.

The present invention is a dental curable composition comprising a curable resin (A), a porous inorganic filler (B), and a polymerization initiator (C), wherein the porous inorganic filler (B) comprises a silicon dioxide and an oxide comprising at least one kind of the other metallic elements, and a ratio $(I_1/I_2)$ of a maximum absorbance $(I_1)$ at 3730 to 3750 $cm^{-1}$ to a maximum absorbance $(I_2)$ at 3000 to 3600 $cm^{-1}$ in, the infrared absorption spectrum of the porous inorganic filler (B) is not less than 1 and not more than 3.

The curable resin (A) which can be used in the dental curable composition of the present invention, may generally utilize the known monofunctional or polyfunctional polymerizable monomers without restriction. A representative example to be generally and preferably used is a polymerizable monomer having an acryloyl group and/or a metacryloyl group. In addition, in the present invention, both of an acryloyl group-containing polymerizable monomer and a metacryloyl group-containing polymerizable monomer are comprehensively represented by (meth)acrylate or (meth)acryroil.

The polymerizable monomer having the acryloyl group and/or metacryloyl group which can be utilized as the curable resin (A) which may be used in the dental curable composition of the present invention, is specifically illustrated as follows:

Examples of the monofunctional monomer include (meth)acrylate esters, such as methyl(meth)acrylate, ethyl(meth)acrylate, butyl(meth)acrylate, hexyl(meth)acrylate, tetrahydrofurfuryl(meth)acrylate, 2-hydroxyethyl(meth)acrylate, glycidyl(meth)acrylate, lauryl(meth)acrylate, cyclohexyl (meth)acrylate, benzyl (meth)acrylate, allyl(meth)acrylate, 2-ethoxyethyl(meth)acrylate, methoxy polyethylene glycol (meth)acrylate, glycerol(meth)acrylate, and isobonyl(meth)acrylate; silane compounds such as γ-(meth)acryloyl oxypropyl trimethoxysilane, and γ-(meth)acryloyl oxypropyl triethoxysilane; and nitrogen-containing compounds such as 2-(N,N-dimethylamino) ethyl (meth)acrylate, N-methylol (meth)acrylamide, and diacetone (meth)acrylamide.

Examples of the aromatic bifunctional monomer include 2,2-bis(4-(meth)acryloyloxy phenyl)propane, 2,2-bis(4-(3-(meth)acryloyloxy-2-hydroxypropoxy)phenyl)propane, 2,2-bis(4-(meth)acryloyloxy ethoxy phenyl)propane, 2,2-bis(4-(meth)acryloyloxydiethoxy phenyl)propane, 2,2-bis(4-(meth)acryloyloxy tetra-ethoxy phenyl)propane, 2,2-bis(4-(meth)acryloyloxypentaethoxy phenyl)propane, 2,2-bis(4-(meth)acryloyloxy dipropoxy phenyl)propane, 2(4-(meth) acryloyloxy ethoxy phenyl)-2(4-(meth)acryloyloxydiethoxy phenyl) propane, 2(4-(meth)acryloyloxy diethoxy phenyl)-2(4-(meth)acryloyloxy triethoxy phenyl) propane, 2(4-(meth)acryloyloxy dipropoxy phenyl)-2(4-(meth)acryloyloxy triethoxy phenyl)propane, 2,2-bis(4-(meth)acryloyloxy dipropoxy phenyl)propane, and 2,2-bis(4-(meth)acryloyloxy isopropoxy phenyl)propane.

Examples of the aliphatic bifunctional monomer includes 2-hydroxy-3-acryloyloxy propyl methacrylate, neopentyl glycol hydroxypivalate di(meth)acrylate, ethylene glycol di(meth)acrylate, diethylene glycol, di(meth)acrylate, triethylene glycol di(meth)acrylate, butylene glycol di(meth)acrylate, neopentyl glycol di(meth)acrylate, propylene glycol di(meth)acrylate, polyethylene glycol di(meth)acrylate, 1,3-butanediol di(meth)acrylate, 1,4-butanediol di(meth(acrylate, 1,6-hexane dioldi(meth)acrylate, and glycerol di(meth)acrylate.

Examples of the trifunctional monomer include trimethylolpropanetri(meth)acrylate, trimethylolethane-tri(meth)acrylate, trimethylolmethanetri(meth)acrylate, and pentaerythritol-di(meth)acrylate.

Examples of the tetrafunctional monomer include pentaerythritoltetra(meth)acrylate, and ditrimethylolpropane-tetra(meth)acrylate.

Examples of the urethane-based polymerizable monomer include di(meth)acrylate, etc., having a bifunctional, trifunctional or higher functional urethane bond and Induced from an adduct of a polymerizable monomer having a hydroxyl group such as 2-hydroxyethyl(meth)acrylate, 2-hydroxypropyl(meth)acrylate, or 3-chloro-2-hydroxypropyl(meth)acrylate, and a diisocyanate compound such as methylcyclohexanediisocyanate, methylenebis(4-cyclohexylisocyanate), hexamethylenediisocyanate, trimethylhexamethylenediisocyanate, isophoronediisocyanate, diisocyanatemethylmethylbenzene, or 4,4-diphenylmethanediisocyanate.

An oligomer or prepolymer having intramolecularly at least one or more polymerizable groups other than the (meth)acrylate-based polymerizable monomer, is freely used without restriction. Moreover, there is no problem even when it has substituent(s) such as a fluoro group, etc. within the same molecule.

The porous inorganic filler (B) in the present invention is shown to be an inorganic filler having at least one or more pores. The existence or absence of the pores in the inorganic filler can be measured, e.g., by a gas adsorption method or mercury intrusion method. More specifically, the porous inorganic filler (B) in the present invention means an inorganic filler, the pore volume of which is measured by the gas adsorption method, is 0.01 cc/g or more.

Although an amorphous or spherical-shape can be used as the shape of the porous inorganic filler (B) in the present invention, the shape is preferably a spherical-shape. By making the spherical shape of the porous inorganic filler (B), excellent surface lubricating property is conferred to the dental curable composition, and the increase in filler content can confer high mechanical strength to the composition.

The shape of the porous inorganic filler (B) in the present invention can be defined by circularity. In the present invention, the spherical shape means that the porous inorganic filler (B) has a circularity of 0.8 or more, and the amorphous shape means that the porous inorganic filler (B) has less than 0.8.

The circularity can be calculated based on the project area and circumference length of particles obtained by observing the inorganic filler with a scanning election microscope (SEM), and treating the observed images by means of an image-analysis equipment. By assuming that the project area of the inorganic filler obtained by the image treatment is represented as S and circumference length of its particles is represented as L, $$Circularity = (4 \times \pi \times S)/(L^2)$$

A reproducible substantial constant value is obtained by averaging with the 100 or more numbers of samples to calculate the value.

The porous inorganic filler (B) in the present invention preferably has a mean particle size in a range of 0.1-10 μm, more preferably 1-8 μm. When the mean particle size exceeds 10 μm, the mechanical strength of the obtained dental curable composition decreases and further the lubricating property of the polished surface of the cured material decreases. Moreover, when the mean particle size is less than 0.1 μm, this is not preferable since decrease in the filling rate of the obtained dental curable composition is caused and its mechanical strength decreases.

For the porous inorganic filler (B) in the present invention, its pore volume is 0.01-1.00 cc/g, preferably 0.10-0.80 cc/g and its specific surface area is 5-500 m$^2$/g, preferably 10-300 m$^2$/g. Such features cause a firm binding in an interface by infiltrating the curable resin into the pores on the surface of the filler. Therefore, the dental curable composition after curing is excellent in mechanical strength, and has a property capable of resisting a strong mechanical stress such as wear with a toothbrush or dental occlusion in addition to bending strength. When the pore volume and/or specific surface area are too small, its mechanical strength and wear resistance are inferior. When the pore volume and/or specific surface area are too large, it is difficult to combine a larger amount of the filler into the curable resin, and accordingly the filling rate of the filler becomes low, and its mechanical strength or wear resistance is inferior.

The porous inorganic filler (B) in the present invention is characterized by comprising a silicon dioxide and an oxide comprising at least one kind of the other metallic elements. An oxide of metallic elements, such as Al, Ba, Bi, Ca, Ce, Co, Cu, Er, Fe, Hf, Ho, In, La, Mg, Mn, Nd, Ni, Pb, Sb, Sn, Sr, Ta, Ti, Y, Yb, Zn and Zr, is used as the at least one kind of the other metallic elements, without restriction. Examples of the preferable metal oxides include an oxide of Al, Ba, Ca, Co, Cu, Fe, Hf, La, Mg, Ni, Sr, Ti, Zn, and Zr. Furthermore, the dental curable composition can have X-ray contrast property by selecting the oxide of metallic elements with a comparatively large atomic number as metallic elements. Oxides of metals such as Ba, Ti and Zr, are used as a metal oxide suitable to provide X-ray contrast property, and Zr is more preferable.

The oxide comprising at least one kind of the other metallic elements contained in the porous inorganic filler is preferably contained at 1 to 30 wt %, more preferably 3 to 20 wt % in terms of the oxide. When the oxide comprising at least one kind of the other metallic elements contained in the porous inorganic filler is contained at not more than 1 wt %, a suitable X-ray contrast property cannot be obtained. When the oxide is contained at not less than 30 wt %, the refractive index of particles is too high and thereby this is not preferable.

In the infrared absorption spectrum of the porous inorganic filler (B) in the present invention, the peak pertaining to 3730 to 3750 cm$^{-1}$ is originated from isolated silanol groups, and the peak pertaining to 3000 to 3600 cm$^{-1}$ is originated from vicinal silanol groups or absorbed water.

The isolated silanol groups generally exhibit high reaction activity in an acidic condition, and have a high reactivity with the silane coupling materials. On the other hand, the vicinal silanol groups have a lower reaction activity as compared with that of the isolated silanol groups, and have a poor reactivity with the silane coupling materials. Moreover, when the absorbed water is excessively included on the surface of the porous inorganic filler (B), a reaction of the silane coupling materials with the surface of the porous inorganic filler (B) is prevented to react between the silane coupling materials and the absorbed water. Therefore, a chemical bonding of the silane coupling materials and the porous inorganic filler (B) is not obtained.

An infrared spectroscopy, etc., are effective to distinguish and quantify the peaks originated from the isolated silanol groups, the vicinal silanol groups, and the absorbed water, and there are KBr tablet method, Nujol method, and a microfilm method as a penetration method of its specific measuring method, and a diffuse reflection method, a multiple reflection (ATR) method, etc., may be used as the reflection method. The diffuse reflection method of the reflection method among them, is especially and preferably used due to easy preparation of samples.

The porous inorganic filler (B) to be used in the dental curable composition of the present invention is characterized in that a ratio ($I_1/I_2$) of a maximum absorbance ($I_1$) of 3730 to 3750 cm$^{-1}$ to a maximum absorbance ($I_2$) of 3000 to 3600 cm$^{-1}$ is not less than 1 and not more than 3 in its infrared absorption spectrum. When the above-mentioned ratio ($I_1/I_2$) is not more than 1, the vicinal silanol groups with low reactivity or the absorbed water which prevents a chemical bonding of the porous inorganic filler (B) with the silane coupling materials become excessive, and a sufficient chemical bonding between the porous inorganic filler (B) and the silane coupling materials is not obtained. Therefore, neither sufficient mechanical property nor durability on aged deterioration cannot be conferred to the dental curable composition. On the other hand, when the isolated silanol groups is silane-coupled to the porous inorganic filler (B) which is contained more than needed, an excessive isolated silanol groups cannot be reacted with the silane coupling materials, and the excessive isolated silanol group remains under their unreactions, and thereby causes a durability decrease in aged deterioration. Moreover, when the above-mentioned ratio ($I_1/I_2$) is not less than 3, the porous inorganic fillers (B) are easily aggregated each other. The dental curable composition comprising the aggregated filler is not preferable since the lubricating property of the polished surface of its cured material decreases in addition to a decrease of mechanical strength. The ratio ($I_1/I_2$) of a maximum absorbance ($I_2$) is preferably not less than 1.2 and not more than 3.0, and more preferably not less than 1.25 and not more than 3.0.

A method for producing the porous inorganic filler (B) to be used in the dental curable composition of the present invention, comprises mixing an acidic silicic acid solution, a silicon dioxide sol and an aqueous metal salt solution of at least one kind of the other metallic elements, and heat-treating dry particles obtained by spray-drying the mixed slurry, wherein the heat-treating is divided into a primary heating and a last heating to process the dry particles.

[Slurry Preparation]

The mean particle size of the silicon dioxide particles of the above-mentioned silicon dioxide sol is preferably within the range of 5 to 50 nm, and in particular, 5 to 30 nm. When the mean particle size is less than 5 nm, the stability of the silicon dioxide sol-containing mixed slurry becomes insufficient. Therefore, adhesion property between the curable resin (A) and the porous inorganic filler (B) may decrease, or refractive index of the porous inorganic filler (B) may increase and transparency of the porous inorganic filler (B) may decrease. The mixed slurry is subjected to the spray drying. On the other hand, when the mean particle size of silicon dioxide particles is more than 50 nm, the strength of the obtained porous inorganic filler (B) becomes insufficient.

Moreover, silicon dioxide particles may be non-porous, or porous, and may be appropriately selected to be used. The concentration of the silicon dioxide sol at this time may be used without restriction as long as the concentration usually ranges from 10 to 50% by weight as converted into $SiO_2$. For the acidic silicic acid solution, a material may be used which is obtained by dealkalization with an ion exchange resin, etc., from an aqueous alkali metal silicate solution, and the concentration of the acidic silicic acid solution may usually range from 1 to 10% by weight, preferably 2 to 5% by weight based on conversion into $SiO_2$.

Appropriately, although the silicon dioxide sol and the acidic silicic acid solution are first mixed, the mixed ratio of the silicon dioxide sol and the acidic silicic acid solution at this time is preferably such that the relationship between $SiO_2$ in the silicon dioxide ($S_Z$) and $SiO_2$ in the acidic silicic acid solution ($S_A$) complies with $S_A/(S_A+S_Z)=0.05$ to 0.70. Namely, the silicon dioxide originated from the acidic silicic acid solution is preferably mixed such that the silicon dioxide is contained at 5 to 70% by weight in all the silicon dioxides.

When the rate of the silicon dioxide originated from the acidic silicic acid solution is less than 5% by weight, effects which control particlization of the oxide, aggregation of particles and also crystallization, may not be acquired, e.g., by reacting silicon dioxide of the silicic acid solution having a low degree of polymerization with oxide(s) other than the silicon dioxide. On one hand, when the rate of the silicon dioxide originated from the acidic silicic acid solution exceeds 70% by weight, there is a tendency that the pore volume of the porous inorganic filler (B) to be obtained becomes small, and thereby adhesion property with curable resin decreases, or transparency of the dental curable composition to be obtained decreases when the refractive index decreases and a difference in refractive index from that of the curable resin (A) increases.

Subsequently, to this mixed slurry, an aqueous metal salt solution of at least one kind of the other metallic elements is added as a source of oxide (s) other than the silicon dioxide. The aqueous metal salt solution is preferably from a nitrate, hydrochloride, sulphate, etc. The aqueous metal salt solution is specifically from zirconium nitrate, zirconium ammonium nitrate, zirconium ammonium carbonate, zirconium chloride, zirconium oxychloride, zirconium sulfate, titanyl sulfate, titanium chloride, barium nitrate, aluminium sulfate, zinc chloride, boric acid, etc.

The concentration of the aqueous metal salt solution in the mixed slurry to which the above-mentioned aqueous metal salt solution is added, is preferably 0.5 to 10% by weight and more preferably 1 to 8% by weight based on conversion into oxides. When the concentration is less than 0.5% by weight, this is not preferable since particles having a particle size of not more than 1 μm increase and their yield decreases. On the other hand, when the concentration exceeds 10% by weight, the viscosity of the mixed slurry becomes high and thereby the stability of the mixed slurry decreases. Moreover, an inorganic filler having a particle size of more than 10 μm increases, its yield also decreases when the inorganic filler is removed, and it is not preferable since transparency of the dental curable composition to be obtained decreases when used as itself.

[Spray Drying]

Next, this mixed slurry is dried. Spray drying is preferable to obtain a spherical inorganic filler. Although there is no special restriction in a spray drying method, a method suitable for obtaining the spherical inorganic filler having a desired size is preferable. For example, there are methods of using various forms of spray dryers, such as disk rotating-type or nozzle-type. Drying conditions can be appropriately selected according to composition, stability, etc. of the mixed slurry. There is no special restriction in the drying method of the mixed slurry to obtain the amorphous inorganic filler.

[Primary Heat-Treatment Process]

Next, the inorganic filler obtained by the spray drying is primarily heat-treated. Although its heat-treatment temperature also varies with the kind and content of an oxide component other than the silicon dioxide and the rate of the silicon dioxide originated from the acidic silicic acid solution, the heat-treatment temperature is preferably within a range of from 200 to 900° C., and more specifically from 500 to 900° C. When the heat-treatment temperature is less than 200° C., the strength of the inorganic filler is insufficient, strength of a cured material of the dental curable composition to be obtained is also low, and there is a tendency that its wear durability is inferior. When the heat-treatment temperature exceeds 900° C., crystallization of metal oxides other than the silicon dioxide may proceed, and the transparency of the cured material of the dental curable composition may decrease. Moreover, sintering of silicon dioxide or metal oxides other than the silicon dioxide may proceed, and strength of a cured material of the dental curable composition may decrease since a desired pore volume or specific surface is not obtained, or its particles are bound together not to obtain a desired particle size. Moreover, when obtaining an amorphous inorganic filler, the above heat-treated product is primarily heat-treated, and pulverized to perform the primary heat, or the dried article is pulverized as a primary heat-treated article. If a desired particle size is obtained, there is no special restriction in a pulverizing method, and a method of using various form of mills, such as ball mill, beads mill, colloid mill, hammer mill, and jet mill, may be used.

[Classification Process]

When particles of not more than 0.1 µm or not less than 10 µm are contained in the inorganic filler obtained, by the above-mentioned primary heat-treatment or pulverizing, an inorganic filler of not more than 0.1 µm and not less than 10 µm is preferably removed by classification. There is no special restriction in the classification procedure as long as an inorganic filler of not more than 0.1 µm and not less than 10 µm can be removed, and examples of the classification include sieving, wet sedimentation, dry type of wind power classification, etc. Among them, wet sedimentation is appropriately used since it has high classification precision. In addition, they are preferably dried when classification is performed by a wet type.

[Final Heat-Treating Process]

By finally performing a heat-treating, a porous inorganic filler (B) can be obtained in which a ratio ($I_1/I_2$) of a maximum absorbance ($I_1$) of 3730 to 3750 $cm^{-1}$ to a maximum absorbance ($I_2$) of 3000 to 3600 $cm^{-1}$ is not less than 1 and not more than 3. Although the heat-treatment temperature varies with the kinds and contents of oxide component(s) other than silicon dioxide, and rates of the silicon dioxide originated from the acidic silicic acid solution, the heat-treatment temperature is preferably within a range of 300 to 900° C. and more preferably 400 to 900° C. When the heat-treatment temperature is less than 300° C., moisture absorbed on the particle surface cannot be removed, and thereby the ratio ($I_1/I_2$) of a maximum absorbance ($I_1$) of 3730 to 3750 $cm^{-1}$ to a maximum absorbance ($I_2$) of 3000 to 3600 $cm^{-1}$ may become not more than 1, and strength of the cured material of the dental curable composition may be low. Moreover, in not less than 900° C., not only absorbed moisture is removed, but isolated silanol groups in 3730 to 3750 $cm^{-1}$ are also removed, and sintering of a silicon dioxide or metal oxides other than the silicon dioxide proceeds, a desired pore volume or specific surface area may not be obtained, or particles are bound not to obtain a desired particle size, and thereby strength of a cured material of the dental curable composition may decrease.

The content of the porous inorganic filler (B) in the dental curable composition in the present invention can be set up in the known range generally used in the dental-material field without restriction. By taking into consideration easy handling and physical properties, the content of the porous inorganic filler (B) is preferably 20 to 99% by weight, and more preferably 40 to 90% by weight in the dental curable composition.

These porous inorganic fillers (B) are preferably treated with the known silane coupling materials, titanate coupling materials, or aluminate coupling materials. Examples of the silane coupling materials include γ-metacryloxy propyltrimethoxy silane, γ-metacryloxy propyltriethoxy silane, etc. The γ-metacryloxy propyltrimethoxy silane is preferably used.

The polymerization initiator (C) is not restricted in particular which can be used in the dental curable composition of the present invention, and known radical generators are used without any restriction. Polymerization catalysts are generally and roughly divided into those (chemical polymerization initiators) which start its polymerization by mixing, just before use; those (thermal polymerization initiators) which start polymerization by heating, and those (photopolymerization initiators) which start polymerization by light irradiation.

Examples of the chemical polymerization initiator include a redox type of polymerization initiator system comprising organic peroxide/amine compound, organic peroxide/amine compound/sulfinate, or organic peroxide/amine compound/borate compound; and an organic metal type polymerization initiator system which reacts with oxygen or water to start polymerization. Sulfinates and borate compounds may also start a polymerization by a reaction with polymerizable monomer(s) having acidic group(s).

Examples of the organic peroxide include benzoyl peroxide, parachlorobenzoyl peroxide, 2,4-dichlorobenzoyl peroxide, acetyl peroxide, lauroyl peroxide, tertiary-butyl peroxide, cumenehydro peroxide, 2,5-dimethyl hexane, 2,5-dihydro peroxide, methylethylketone peroxide, and tertiary-butyl peroxybenzoate.

The amine compound is preferably a secondary or tertiary amine formed by an amino group bonded to an aryl group, and specific examples thereof include p-N,N-dimethyl-toluidine, N,N-dimethylaniline, N-β-hydroxyethyl-aniline, N,N-di(β-hydroxyethyl)-aniline, p-N,N-di(β-hydroxyethyl)-toluidine, N-methyl-aniline, and p-N-methyl-toluidine.

Specific examples of the sulfinate include sodium benzenesulfinate, lithium benzenesulfinate/and sodium p-toluenesulfinate.

Examples of the borate compound include sodium salts, lithium salts, potassium salts, magnesium salts, tetrabutylammonium salts, and tetramethylammonium salts of trialkylphenylboronate and trialkyl(p-phlorophenyl)borate (wherein alkyl groups are an n-butyl group, an n-octyl group, an n-dodecyl group, etc.).

Examples of the organic metal type polymerization initiator include organic boron compounds such as triphenylborane, tributylborane, and a partially oxidized tributylborane.

On the other hand, examples of the photopolymeric initiator include a material including a photosensitization agent, and a photosensitization agent/photopolymerization accelerator. Specific examples of the photosensitization agent include α-diketones such as benzil, camphorquinone, α-naphthyl, acetonaphthene, p,p'-dimethoxybenzil, p,p'-dichlorobenzilacetyl, petanedione, 1,2-phenanthrenequinone, 1,4-phenanthrenequinone, 3,4-phenanthrenequinone, 9,10-phenanthrenequinone, and naphthoquinone; benzoinalkylethers such as benzoin, benzoinmethylether, and benzoinethylether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone; benzophenones such as benzophenone, p-chlorobenzophenone, and p-methoxybenzophenone; acylphosphine oxides such as 2,4,6-trimethylbenzoyldiphenyl-phosphine oxide and bis(2,6-dimethoxybenzoyl)-2,4,4-trimethylpentyl-phosphine oxide; α-aminoacetophenones such as 2-benzyl-dimethylamino-1-(4-morpholinophenyl)-butanone-1, and 2-benzyl-diethylamino-1-(4-morpholinophenyl)-propanone-1; ketals such as benzyldimethylketal, benzyldiethylketal, and benzyl(2-methoxyethylketal), and titanocenes such as bis(cyclopentadienyl)-bis (2,6-difluoro-3-(1-pyrrolyl)phenyl)-titanium, bis(cyclopentadienyl)-bis (pentanefluorophenyl)-titanium, and bis(cyclopentadienyl)-bis(2,3,5,6-tetrafluro-4-disiloxyphenyl)-titanium.

Specific examples of the photopolymerization agent include tertiary amines such as N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-diroethylaniline, m-chloro-N,N-dimethylaniline, p-dimethylaminobenzaldehyde, p-dimethylaminoacetophenone, p-dimethylaminobenzoic acid, p-dimethylamino-benzoic acid-ethylester, p-dimethylamino-benzoic acid-aminoester, N/N-dimethyl-anthranilic acid-methylester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethylmethacrylate, N,N-diethylaminoethylmethacrylate, and 2,2'-(n-butylimino) diethanol; secondary amines such as N-phenylglycine; barbituric acids such as S-butyl-barbituric acid, and 1-benzyl-5-phenyl-barbituric acid; tin compounds such as dibutyltin-diacetate, dibutyltin-dilaurate, dioctyltin-dilaurate, dioctyltin-didecanoate, dioctyltin-bis(mercaptoacetic acid-isooctylester)salt, and tetramethyl-1,3-diacetoxydistanoxane; aldehyde compounds such as laurylaldehyde and terephthalaldehyde; and sulfur-including compounds such as dodecylmercaptan, 2-mercaptobenzoxazole, 1-decanethiol, and thiosalicylic acid.

To improve the photopolymerization acceleration capacity, addition of oxycarboxylic acids, such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid, and dimethylolpropionic acid, is furthermore effective in addition to the photopolymerization accelerators.

Each of these polymeric initiators alone or some thereof in combination is/are usable regardless of the polymerization type and the polymerization method. No problem arises from these polymeric initiators even when a secondary processing is applied to any of the polymeric initiators as necessary such as encapsulation thereof in micro capsules.

Although the content of the polymerization initiator to be used in the dental curable composition of the present invention can be appropriately selected according to the use, the content is preferably within a range of 0.01 to 10 parts by weight, more preferably a range of 0.1 to 5 parts by weight.

EXAMPLES

Although Examples of the present invention are specifically described below, the present invention is not intended to be limited to these Examples. The test methods in Examples and Comparative Examples are described as follows:

(1) Composition Analysis of Porous Inorganic Filler (B)

Purposes: Composition Analysis Measurement of the Porous Inorganic Filler (B)

Methods: The composition analysis of the porous inorganic filler (B) was measured with a fluorescent x-ray equipment. The combination ratio of the various metallic elements in the porous inorganic filler (B) was calculated with oxide conversion.

(2) Shape Measurement of Porous Inorganic Filler (B)

Purposes: Shape Measurement of the Porous Inorganic Filler (B)

Methods: The shape of the porous inorganic filler (B) was confirmed from its photography image of a scanning election microscope (hereinafter referred to as "SEM"). A mean particle size, the coefficient of variation of particle size and its circularity are obtained by processing the photography image of the above-mentioned SEM with the image-analysis equipment. The number of samples processed by their images is not less than 100. In addition, the circularity defined herein is determined by image-processing the photography image in SEM. Namely, by defining the area of the particles obtained with the image processing as S and the circumference length of particles as L, $$\text{Circularity}=(4\times\pi\times S)/(L2)$$

Moreover, circle equivalent diameter=$(4\times S/\pi)^{1/2}$ were used as the particle size. The shape of the porous inorganic filler (B) having a circularity of not less than 0.8 was defined as a spherical shape, whereas the shape of the porous inorganic filler (B) having a circularity of less than 0.8 was defined as an amorphous shape.

(3) Infrared Absorption Spectrum Measurement

Purposes: Measurement of the Infrared Absorption Spectrum by a Diffuse Reflection Method Methods: The infrared absorption spectrum was measured with the diffuse reflection method of the infrared absorption spectrometer (JASCO FT-IR-6300, manufactured by JASCO Corp.) (measuring range: 400 to 8000 cm$^{-1}$ under nitrogen atmosphere). The maximum absorbance ($I_1$) of 3730 to 3750 cm$^{-1}$ and the maximum absorbance ($I_2$) of the peak pertaining to 3000 to 3600 cm$^{-1}$ were calculated from the obtained spectrum.

(4) Contrast Ratio Measurement

Purposes: Evaluation of Contrast Ratio (Transparency) in a Cured Body of the Dental Composition.

Methods: After filling up a metallic mold made from stainless steel (15 mm in diameter×1 mm in thickness) with a composition to be subjected to the test, covergrasses are placed at both sides of the metallic mold and pressure-welded with the metallic mold. In the measurement after curing, the photopolymerization irradiator (Solidilite: manufactured by SHOFU, Inc.) is used to cure the front surface and the back surface of the composition by light-irradiating them for 3 minutes each. A test sample is color-measured with a spectrum chromatometer (manufactured by Konica Minolta Co., Ltd.). Y value upon color-measuring when a white board is placed under the cured body is defined as $Y_W$, and Y value upon color-measuring when a black board is placed under a cured body is defined as $Y_B$. The transparency of the cured body was evaluated by assuming C value=$Y_B/Y_W$ as a contrast ratio. The material is more transparent when C value approaches 0, and the material is more opaque when C value approaches 1. The contrast ratio is preferably 0.50 or less to reproduce the color tone of natural teeth.

(5) Bending Strength Test

Purposes: Evaluation of Bending Strength for Cured Materials

Methods: After filling up a metallic mold made from stainless steel (25×2×2 mm: rectangular parallelepiped type) with a composition to be subjected to the test, covergrasses are placed at both sides of the metallic mold and pressure-welded with a glass slab. Subsequently, a photopolymerization irradiator (Solidilite: manufactured by SHOFU, Inc.) is used to cure the front surface and the back surface of the composition by light-irradiating them for 3 minutes each. A cured material was removed from the metallic mold after curing, and a cured material immersed into water at 37° C. for 24 hours was used as the test sample (first stage). Further, in order to evaluate durability by aged deterioration, the above-mentioned test sample is subjected to a thermal cycle test (in water at 4° C. to 60° C., immersion during 1 minute each, 2000 times), and subsequently a measurement of bending strength (after thermal cycling) was performed. Measurement of bending strength in this test is performed with Instron Universal Testing Machine (Instron 5567: manufactured by Instron company) and at a distance between fulcrums of 20 mm and a crosshead speed of 1 mm/min. The bending strength measurements were performed at the initial and after the thermal cycling to calculate a strength maintenance rate under a durability to aged deterioration according to the following formula:

Bending strength maintenance rate=(initial bending strength)/(bending strength after thermal cycling)×100

(Preparation of Binder Resin)

Seventy parts by weight of a di(methacryloxyethyl)trimethylhexamethylene diurethane (UDMA), 30 parts by weight of triethyleneglycol dimethacrylate (3G), 0.3 parts by weight of camphor quinone, and 2 parts by weight of dimethylamino ethylmethacrylate were mixed to produce a binder resin (A-1).

Seventy parts by weight of 2,2-bis(4-(3-metacryloyloxy-2-hydroxypropoxy) phenyl)propane (Bis-GMA), 30 parts by weight of triethyleneglycol dimethacrylate (3G), 0.3 parts by weight of camphor quinone, and 2 parts by weight of dimethylamino ethylmethacrylate were mixed to produce a binder resin (A-2).

(Production Method of Inorganic Fillers (Classified Dry Products and Pulverized Products))

Production Method 1 ($ZrO_2$: 18% by Weight)

To 1,867 g of a silicon dioxide sol in which a silicon dioxide sol (manufactured by JGC Catalysts and Chemicals Ltd., CATALOID S-20L, a mean particle size of 17 nm, 10% by weight of $SiO_2$) was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGC Si-Tech Co., Ltd.), its dealkalization was performed by using a strongly acidic cation exchange resin (H type of SK1B, manufactured by Mitsubishi Chemical, Inc.) to prepare 525 g of an acidic silicic acid solution at a concentration of 3.0% by weight as $SiO_2$. This acidic silicic acid solution was mixed with the diluted silicon dioxide sol adjusted of pH, 41 g of an aqueous NaOH solution at a concentration of 3% by weight was added to prepare a mixed slurry of the acidic silicic acid solution and the silicon dioxide sol, adjusted to pH of 9.6. To this, 394 g of an aqueous zirconium ammonium carbonate solution diluted with water was added as a component other than the silicon dioxide such that a zirconium ammonium carbonate (manufactured by Daiichi Kigenso Kagaku Xogyo Co., Ltd.: Zircosol AC-7, $ZrO_2$: 13% by weight) becomes 4% by weight as $ZrO_2$, and then agitated for 15 min to prepare a mixed slurry. Subsequently, spray drying was performed with a disk type spray dryer under a condition of an entrance temperature of 30° C., and an outlet temperature of 50° C. for hot air, and a supply rate of 200 g/min of the mixed slurry. The resultant powder was dried at 110° C. for 15 hours, and subsequently heat-treated at 650° C. for 3 hours (primary heat-treatment) to prepare a primary heat-treated product. Then, wet sedimentation was performed by using an absolute ethanol (traceable 99 primary, manufactured by Japan Alcohol Co., Ltd.) and dried at 110° C. for 5 hours to prepare a classified dry product (1).

Particle size was measured with a laser diffraction dispersion type particle size distribution measuring equipment (SALD-200VER manufactured by Shimadzu Corp.), and their pore volume and specific surface area were measured by using $N_2$ gas adsorption method by BELSORP-mini II manufactured by BEL Japan, Inc. The resultant classified dry product (1) had particle size: 2.9 μm, specific surface area: 170 m²/g and pore volume: 0.22 cm³/g. In addition, the specific surface area was calculated by a BET method.

Production Method 2 ($ZrO_2$: 14% by Weight)

To 1,867 g of a silicon dioxide sol in which diluted the silicon dioxide sol (manufactured by JGC Catalysts and Chemicals Ltd.: CATALOID S-20L, a mean particle size of 17 nm, 10% by weight of $SiO_2$) was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGC Si-Tech Co., Ltd.), its dealkalization was performed by using a strongly acidic cation exchange resin (H type of SK1B, manufactured by Mitsubishi Chemical, Inc.) to prepare 1,001 g of an acidic silicic acid solution at a concentration of 3.0% by weight as $SiO_2$. This acidic silicic acid solution was mixed with the diluted silicon dioxide sol adjusted of pH, 56 g of an aqueous NaOH solution at a concentration of 3% by weight was added to prepare a mixed slurry of the acidic silicic acid solution and the silicon dioxide sol, adjusted to pH of 9.6. To this, 350 g of an aqueous zirconium ammonium carbonate solution diluted with water was added as a component other than the silicon dioxide such that a zirconium ammonium carbonate (manufactured by Daiichi Kigenso Kagaku Xogyo Co., Ltd.: Zircosol AC-7, $ZrO_2$: 13% by weight) becomes 4% by weight as $ZrO_2$, and then agitated for 15 min to prepare a mixed slurry. Subsequently, the same method as that of Production method 1 was performed to prepare a classified dry product (2).

The resultant classified dry product (2) had particle size: 2.9 μm, specific surface area: 151 m²/g and pore volume: 0.18 cm³/g.

Production Method 3 ($ZrO_2$: 5% by Weight)

To 1,867 g of a silicon dioxide sol in which a silicon dioxide sol (manufactured by JGC Catalysts and Chemicals Ltd.: CATALOID S-20L, a mean particle size of 17 nm, 10% by weight of $SiO_2$) was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGC Si-Tech Co., Ltd.), its dealkalization was performed by using a strongly acidic cation exchange resin (H type of SK1B, manufactured by Mitsubishi Chemical, Inc.) to prepare 862 g of an acidic silicic acid solution at a concentration of 3.0% by weight as $SiO_2$. This acidic silicic acid solution was mixed with the diluted silicon dioxide sol adjusted of pH, 51 g of an aqueous NaOH solution at a concentration of 3% by weight was added to prepare a mixed slurry of the acidic silicic acid solution and the silicon dioxide sol, adjusted to pH of 9.6. To this, 108 g of an aqueous zirconium ammonium carbonate solution diluted with water was added as a component other than the silicon dioxide such that a zirconium ammonium carbonate (manufactured by Daiichi Kigenso Kagaku Xogyo Co., Ltd.: Zircosol AC-7, $ZrO_2$: 13% by weight) becomes 4% by weight as $ZrO_2$, and then agitated for 15 min to prepare a mixed slurry. Subsequently, the same method as that of Production method 1 was performed to prepare a classified dry product (3).

The resultant classified dry product (3) had particle size: 2.9 μm, specific surface area: 175 m$^2$/g and pore volume: 0.21 cm$^3$/g.

Production Method 4 ($ZrO_2$: 35% by Weight)

To 1,867 g of a silicon dioxide sol in which a silicon dioxide sol (manufactured by JGC Catalysts and Chemicals Ltd.: CATALOID S-20L, a mean particle size of 17 nm, 10% by weight of $SiO_2$) was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGC Si-Tech Co., Ltd.), its dealkalization was performed by using a strongly acidic cation exchange resin (H type of SK1B, manufactured by Mitsubishi Chemical, Inc.) to prepare 340 g of an acidic silicic acid solution at a concentration of 3.0% by weight as $SiO_2$. This acidic silicic acid solution was mixed with the diluted silicon dioxide sol adjusted of pH, 35 g of an aqueous NaOH solution at a concentration of 3% by weight was added to prepare a mixed slurry of the acidic silicic acid solution and the silicon dioxide sol, adjusted to pH of 9.6. To this, 889 g of an aqueous zirconium ammonium carbonate solution diluted with water was added as a component other than the silicon dioxide such that a zirconium ammonium carbonate (manufactured by Daiichi Kigenso Kagaku Xogyo Co., Ltd.: Zircosol AC-7, $ZrO_2$: 13% by weight) becomes 4% by weight as $ZrO_2$, and then agitated for 15 min to prepare a mixed slurry. Subsequently, the same method as that of Production method 1 was performed to prepare a classified dry product (4).

The resultant classified dry product (4) had particle size: 2.9 μm, specific surface area: 149 m$^2$/g and pore volume: 0.17 cm$^3$/g.

Production Method 5 ($ZrO_2$: 0.5% by Weight)

To 1,867 g of a silicon dioxide sol in which a silicon dioxide sol (manufactured by JGC Catalysts and Chemicals Ltd.: CATALOID S-20L, a mean particle size of 17 nm, 10% by weight of $SiO_2$) was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGC Si-Tech Co., Ltd.), its dealkalization was performed by using a strongly acidic cation exchange resin (H type of SK1B, manufactured by Mitsubishi Chemical, Inc.) to prepare 1,254 g of an acidic silicic acid solution at a concentration of 3.0% by weight as $SiO_2$. This acidic silicic acid solution was mixed with the diluted silicon dioxide sol adjusted of pH, 87 g of an aqueous NaOH solution at a concentration of 3% by weight was added to prepare a mixed slurry of the acidic silicic acid solution and the silicon dioxide sol, adjusted to pH of 9.6. To this, 11 g of an aqueous zirconium ammonium carbonate solution diluted with water was added as a component other than the silicon dioxide such that a zirconium ammonium carbonate (manufactured by Daiichi Kigenso Kagaku Xogyo Co., Ltd.: Zircosol AC-7, $ZrO_2$: 13% by weight) becomes 4% by weight as $ZrO_2$, and then agitated for 15 min to prepare a mixed slurry. Subsequently, the same method as that of Production method 1 was performed to prepare a classified dry product (5).

The resultant classified dry product (5) had particle size: 2.9 μm, specific surface area: 161 m$^2$/g and pore volume: 0.19 cm$^3$/g.

Production Method 6 ($TiO_2$: 6% by Weight)

To 1,867 g of a silicon dioxide sol in which a silicon dioxide sol (manufactured by JGC Catalysts and Chemicals Ltd.: CATALOID S-20L, a mean particle size of 17 nm, 10% by weight of $SiO_2$, was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGO Si-Tech Co., Ltd.), its dealkalization was performed by using a strongly acidic cation exchange resin (H type of SK1B, manufactured by Mitsubishi Chemical, Inc.) to prepare 873 g of an acidic silicic acid solution at a concentration of 3.0% by weight as $SiO_2$. This acidic silicic acid solution was mixed with the diluted silicon dioxide sol adjusted of pH, 52 g of an aqueous NaOH solution at a concentration of 3% by weight was added to prepare a mixed slurry of the acidic silicic acid solution and the silicon dioxide sol, adjusted to pH of 9.6. To this, 132 g of an aqueous titanyl sulfate solution diluted with water was added as a component other than the silicon dioxide such that a titanyl sulfate dihydrate (manufactured by TAYCA Corp.) becomes 4% by weight as $TiO_2$, and then agitated for 15 min to prepare a mixed slurry. Subsequently, the same method as that of Production method 1 was performed to prepare a classified dry product (6).

The resultant classified dry product (6) had particle size: 2.9 μm, specific surface area: 173 m$^2$/g and pore volume: 0.21 cm$^3$/g.

Production Method 7 ($TiO_2$: 3% by Weight)

To 1,867 g of a silicon dioxide sol in which a silicon dioxide sol (manufactured by JGC Catalysts and Chemicals Ltd.; CATALOID S-20L, a mean particle size of 17 nm, 10% by weight of $SiO_2$) was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGC Si-Tech Co., Ltd.), its dealkalization was performed by using a strongly acidic cation exchange resin (H type of SK1B, manufactured by Mitsubishi Chemical, Inc.) to prepare 833 g of an acidic silicic acid solution at a concentration of 3.0% by weight as $SiO_2$. This acidic silicic acid solution was mixed with the diluted silicon dioxide sol adjusted of pH, 50 g of an aqueous NaOH solution at a concentration of 3% by weight was added to prepare a mixed slurry of the acidic silicic acid solution and the silicon dioxide sol, adjusted to pH of 9.6. To this, 62 g of an aqueous titanyl sulfate solution diluted with water was added as a component other than the silicon dioxide such that titanyl sulfate dihydrate (manufactured by TAYCA Corp.) becomes 4% by weight as $TiO_2$, and then agitated for 15 min to prepare a mixed slurry. Subsequently, the same method as that of Production method 1 was performed to prepare a classified dry product (7).

The resultant classified dry product (7) had particle size: 2.9 μm, specific surface area: 180 m²/g and pore volume: 0.22 cm³/g.

Production Method 8 (BaO: 12% by Weight)

To 1,867 g of a silicon dioxide sol in which a silicon dioxide sol (manufactured by JSC Catalysts and Chemicals Ltd.: CATALOID S-20L, a mean particle size of 17 nm, 10% by weight of $SiO_2$) was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGC Si-Tech Co., Ltd.), its dealkalization was performed by using a strongly acidic cation exchange resin (H type of SK1B, manufactured by Mitsubishi Chemical, Inc.) to prepare 965 g of an acidic silicic acid solution at a concentration of 3.0% by weight as $SiO_2$. This acidic silicic acid solution was mixed with the diluted silicon dioxide sol adjusted of pH, 55 g of an aqueous NaOH solution at a concentration of 3% by weight was added to prepare a mixed slurry of the acidic silicic acid solution and the silicon dioxide sol, adjusted to pH of 9.6. To this, 287 g of an aqueous barium nitrate solution diluted with water was added as a component other than the silicon dioxide such that barium nitrate (manufactured by Wako Pure Chemical Industries, Ltd.) becomes 4% by weight as BaO, and then agitated for 15 min to prepare a mixed slurry. Subsequently, the same method as that of Production method 1 was performed to prepare a classified dry product (8).

The resultant classified dry product (8) had particle size: 2.9 μm, specific surface area: 157 m²/g and pore volume: 0.18 cm³/g.

Production Method 9 (BaO: 7% by Weight)

To 1,867 g of a silicon dioxide sol in which a silicon dioxide sol (manufactured by JGC Catalysts and Chemicals Ltd.: CATALOID S-20L, a mean particle size of 17 nm, 10% by weight of $SiO_2$) was diluted to a concentration of 3% by weight as $SiO_2$, 35 g of an aqueous NaOH solution at a concentration of 3% by weight was added to adjust pH at 9.6. Moreover, after preparing an aqueous sodium silicate solution (diluted water glass) at a concentration of 3.0% by weight as $SiO_2$ by diluting water glass (No. 3 sodium silicate manufactured by AGC Si-Tech Co., Ltd.), its dealkalization was performed by using a strongly acidic cation exchange resin (H type of SK1B, manufactured by Mitsubishi Chemical, Inc.) to prepare 889 g of an acidic silicic acid solution at a concentration of 3.0% by weight as $SiO_2$. This acidic silicic acid solution was mixed with the diluted silicon dioxide sol adjusted of pH, 52 g of an aqueous NaOH solution at a concentration of 3% by weight was added to prepare a mixed slurry of the acidic silicic acid solution and the silicon dioxide sol, adjusted to pH of 9.6. To this, 154 g of an aqueous barium nitrate solution diluted with water was added as a component other than the silicon dioxide such that barium nitrate (manufactured by Wako Pure Chemical Industries, Ltd.) becomes 4% by weight as BaO, and then agitated for 15 min to prepare a mixed slurry. Subsequently, the same method as that of Production method 1 was performed to prepare a classified dry product (9).

The resultant classified dry product (9) had particle size: 2.9 μm, specific surface area: 170 m²/g and pore volume: 0.21 cm³/g.

Production Method 10

The classified dry product (1) was pulverized in a rotating ball mill for 2 hours to prepare a pulverized product (1).

For the classified dry products and the pulverized products prepared with the above-mentioned production methods, the following treatments were performed and they were used in Examples and Comparative Examples. The treatment methods and the properties of porous inorganic fillers used by Examples and Comparative Examples are shown below.

Porous Inorganic Filler (B-1)

The classified dry product (1) obtained with the production method 1 was calcinated at 400° C. for 3 hours in Ring Furnace (Denken Co., Ltd). The resultant filler was porous spherical (circularity: 0.96, particle size: 2.8 μm, specific surface area: 170 m²/g, pore volume: 0.22 cc/g).

Porous Inorganic Filler (B-2)

The classified dry product (1) obtained with the production method 1 was calcinated at 800° C. for 3 hours Ring Furnace (Denken Co., Ltd). The resultant filler was porous spherical (circularity: 0.96, particle size: 2.8 μm, specific surface area: 152 m²/g, pore volume: 0.21 cc/g).

Porous Inorganic Filler (B-3)

The classified dry product (1) obtained with the production method 1 was calcinated at 800° C. for 1 hour in Ring Furnace (Denken Co., Ltd). The resultant filler was porous spherical (circularity: 0.96, particle size: 2.8 μm, specific surface area: 164 m²/g, pore volume: 0.22 cc/g).

Porous Inorganic Filler (B-4)

The classified dry product (2) obtained with the production method 2 was calcinated at 600° C. for 3 hours in Ring Furnace (Denken Co., Ltd). The resultant filler was porous spherical (circularity: 0.96, particle size: 2.8 μm, specific surface area: 151 m²/g, pore volume: 0.18 cc/g).

Porous Inorganic Filler (B-5)

The classified dry product (3) obtained with the production method 3 was calcinated at 600° C. for 3 hours in Ring Furnace (Denken Co., Ltd). The resultant filler was porous spherical (circularity: 0.96, particle size: 2.8 μm, specific surface area: 175 m²/g, pore volume: 0.21 cc/g).

Porous Inorganic Filler (B-6)

The classified dry product (6) obtained with the production method 6 was calcinated at 600° C. for 1 hour in Ring Furnace (Denken Co., Ltd). The resultant filler was porous spherical (circularity: 0.96, particle size: 2.8 μm, specific surface area: 173 m²/g, pore volume: 0.21 cc/g).

Porous Inorganic Filler (B-7)

The classified dry product (7) obtained with the production method 7 was calcinated at 800° C. for 1 hour in Ring Furnace (Denken Co., Ltd). The resultant filler was porous spherical (circularity: 0.96, particle size: 2.8 μm, specific surface area: 174 m²/g, pore volume: 0.22 cc/g).

Porous Inorganic Filler (B-8)

The classified dry product (8) obtained with the production method 8 was calcinated at 600° C. for 3 hours in Ring Furnace (Denken Co., Ltd). The resultant filler was porous spherical (circularity: 0.97, particle size: 2.8 μm, specific surface area: 157 m²/g, pore volume: 0.18 cc/g).

Porous Inorganic Filler (B-9)

The classified dry product (9) obtained with the production method 9 was calcinated at 600° C. for 3 hours in Ring Furnace (Denken Co., Ltd). The resultant filler was porous spherical (circularity: 0.97, particle size: 2.8 μm, specific surface area: 170 m²/g, pore volume: 0.21 cc/g).

Porous Inorganic Filler (B-10)

The classified dry product (1) obtained with the production method 1 was calcinated at 900° C. for 1 hour in Ring Furnace (Denken Co., Ltd). The resultant filler was porous spherical (circularity: 0.96, particle size: 3.5 μm, specific surface area: 81 m²/g, pore volume: 0.13 cc/g).

Porous Inorganic Filler (B-11)

The pulverized product (1) obtained with the production method 10 was calcinated at 700° C. for 3 hours in Ring Furnace (Denken Co., Ltd). The resultant filler was a porous amorphous (circularity: 0.75, particle size: 2.1 μm, specific surface area: 163 m$^2$/g, pore volume: 0.22 cc/g).

Non-Porous Inorganic Filler (B-12)

The classified dry product (1) obtained with the production method 1 was calcinated at 950° C. for 3 hours in the electric furnace. The resultant filler was non-porous spherical (circularity: 0.90, particle size: 1.9 μm, specific surface area: 1 m$^2$/g, and pore volume: less than 0.01 cc/g).

Porous Inorganic Filler (B-13)

The classified dry product (4) obtained with the production method 4 was calcinated at 600° C. for 1 hour in Ring Furnace (Denken Co., Ltd). The resultant filler was porous spherical (circularity: 0.96, particle size: 2.8 μm, specific surface area: 149 m$^2$/g, pore volume: 0.17 cc/g).

Porous Inorganic Filler (B-14)

The classified dry product (5) obtained with the production method 5 was calcinated at 600° C. for 1 hour in Ring Furnace (Denken Co., Ltd). The resultant filler was porous spherical (circularity: 0.96, particle size: 2.8 μm, specific surface area: 161 m$^2$/g, pore volume: 0.19 cc/g).

Silica Micro Bead P-500

Silica Micro Bead P-500 (manufactured by JGC Catalysts and Chemicals Ltd.) was porous spherical (circularity: 0.96, particle size: 1.7 μm, and specific surface area: 130 m$^2$/g, pore volume: 0.25 cc/g).

Silica Filler FUSELEX X

Silica Filler FUSELEX X (Tatsumori, Inc.) was non-porous amorphous (circularity: 0.51, particle size: 3.0 μm, specific surface area: 7.96 m$^2$/g, pore volume: less than 0.01 cc/g).

Production methods of the dental curable compositions used in Examples and Comparative Examples are shown below.

Example 1

A surface treatment was performed with γ-metacryloxy propyltrimethoxy silane to the porous inorganic filler (B-1). By using a double planetary mixer, 59 parts by weight of the surface-treated filler, 1 part by weight of AEROSIL R-972 (hydrophobized ultrafine particle silicon dioxide), and 40 parts by weight of the binder resin (A-1) were kneaded and vacuum-degassed to obtain a dental curable composition.

Example 2

A surface treatment for the porous inorganic filler (B-2) was performed by the same method as that of Example 1. This surface-treated filler was used to obtain a dental, curable composition by the same method as that of Example 1.

Example 3

A surface treatment for the porous inorganic filler (B-3) was performed by the same method as that of Example 1. This surface-treated filler was used to obtain a dental curable composition by the same method as that of Example 1.

Example 4

A surface treatment for the porous inorganic filler (B-4) was performed by the same method as that of Example 1. This surface-treated filler was used to obtain a dental curable composition by the same method as that of Example 1.

Example 5

A surface treatment for the porous inorganic filler (B-5) was performed by the same method as that of Example 1. This surface-treated filler was used to obtain a dental curable composition by the same method as that of Example 1.

Example 6

A surface treatment for the porous inorganic filler (B-6) was performed by the same method as that of Example 1. This surface-treated filler was used to obtain a dental curable composition by the same method as that of Example 1.

Example 7

A surface treatment for the porous inorganic filler (B-7) was performed by the same method as that of Example 1. This surface-treated filler was used to obtain a dental curable composition by the same method as that of Example 1.

Example 8

A surface treatment for the porous inorganic filler (B-8) was performed by the same method as that of Example 1. This surface-treated filler was used to obtain a dental curable composition by the same method as that of Example 1.

Example 9

A surface treatment for the porous inorganic filler (B-9) was performed by the same method as that of Example 1. This surface-treated filler was used to obtain a dental curable composition by the same method as that of Example 1.

Example 10

A surface treatment for the porous inorganic filler (B-10) was performed by the same method as that of Example 1. This surface-treated filler was used to obtain a dental curable composition by the same method as that of Example 1.

Example 11

A surface treatment for the porous inorganic filler (B-11) was performed by the same method as that of Example 1. By using a double planetary mixer, 59 parts by weight of the surface-treated filler, 1 part by weight of AEROSIL R-972 (hydrophobized ultrafine particle silicon dioxide), and 40 parts by weight of the binder resin (A-2) were kneaded and vacuum-degassed to obtain a dental curable composition.

Example 12

A surface treatment for the porous inorganic filler (B-1) was performed by the same method as that of Example 1. This filler was used to obtain a dental curable composition by the same method as that of Example 11.

Comparative Example 1

A surface treatment for the classified dry product (1) was performed with γ-metacryloxy propyltrimethoxy silane.

This filler was used to obtain a dental curable composition by the same method as that of Example 1.

Comparative Example 2

A surface treatment for the porous inorganic filler (B-12) was performed with γ-metacryloxy propyltrimethoxy silane. This surface-treated filler was used to obtain a dental curable composition by the same method as that of Example 1.

Comparative Example 3

A surface treatment for the porous inorganic filler (B-13) was performed with γ-metacryloxy propyl trimethoxy silane. This surface-treated filler was used to obtain a dental curable composition by the same method as that of Example 1.

Comparative Example 4

A surface treatment for the porous inorganic filler (B-14) was performed with γ-metacryloxy propyltrimethoxy silane. This surface-treated filler was used to obtain a dental curable composition by the same method as that of Example 1.

Comparative Example 5

A surface treatment for Silica Micro Bead P-500 was performed with γ-metacryloxy propyltrimethoxy silane. This surface-treated filler was used to obtain a dental curable composition by the same method as that of Example 1.

Comparative Example 6

A surface treatment for FUSELEX X was performed with γ-metacryloxy propyltrimethoxy silane. This surface-treated filler was used to obtain a dental curable composition by the same method as that of Example 1.

The characteristic test results of the dental curable compositions prepared by Examples and Comparative Examples are shown in Table 1.

TABLE 1A

| | | Example 1 | Example 2 | Example 3 | Example 4 | Example 5 | Example 6 |
|---|---|---|---|---|---|---|---|
| Binder resins | | A-1 | A-1 | A-1 | A-1 | A-1 | A-1 |
| Inorganic fillers (B) | Names | B-1 | B-2 | B-3 | B-4 | B-5 | B-6 |
| | Shapes | spherical porous | spherical porous | spherical porous | spherical porous | spherical porous | spherical porous |
| | Compositions | $SiO_2/ZrO_2$ | $SiO_2/ZrO_2$ | $SiO_2/ZrO_2$ | $SiO_2/ZrO_2$ | $SiO_2/ZrO_2$ | $SiO_2/TiO_2$ |
| | Combination ratios (mass %) | 82/18 | 82/18 | 82/18 | 86/14 | 95/5 | 94/6 |
| | $I_1$ | 0.85 | 1.24 | 1.00 | 1.28 | 0.65 | 1.29 |
| | $I_2$ | 0.66 | 0.61 | 0.36 | 0.55 | 0.45 | 0.53 |
| | $I_1/I_2$ | 1.28 | 2.03 | 2.78 | 2.33 | 1.44 | 2.43 |
| Contrast ratios | | 0.19 | 0.19 | 0.19 | 0.25 | 0.45 | 0.25 |
| Bending strength | Initial (MPa) | 145 | 151 | 159 | 152 | 153 | 144 |
| | After thermal cycling (MPa) | 144 | 148 | 148 | 144 | 141 | 132 |
| | Maintenance rate of bending strengths (%) | 99.3 | 98.0 | 93.1 | 94.8 | 92.0 | 91.7 |

| | | Example 7 | Example 8 | Example 9 | Example 10 | Example 11 | Example 12 |
|---|---|---|---|---|---|---|---|
| Binder resins | | A-1 | A-1 | A-1 | A-1 | A-2 | A-2 |
| Inorganic fillers (B) | Names | B-7 | B-8 | B-9 | B-10 | B-11 | B-1 |
| | Shapes | spherical porous | spherical porous | spherical porous | spherical porous | amorphous porous | spherical porous |
| | Compositions | $SiO_2/TiO_2$ | $SiO_2/BaO$ | $SiO_2/BaO$ | $SiO_2/ZrO_2$ | $SiO_2/ZrO_2$ | $SiO_2/ZrO_2$ |
| | Combination ratios (mass %) | 97/3 | 88/12 | 93/7 | 82/18 | 82/18 | 82/18 |
| | $I_1$ | 0.45 | 2.34 | 0.38 | 0.59 | 1.13 | 0.85 |
| | $I_2$ | 0.29 | 0.82 | 0.28 | 0.20 | 0.45 | 0.66 |
| | $I_1/I_2$ | 1.55 | 2.85 | 1.35 | 2.95 | 2.51 | 1.28 |
| Contrast ratios | | 0.45 | 0.34 | 0.47 | 0.19 | 0.30 | 0.30 |
| Bending strength | Initial (MPa) | 142 | 147 | 139 | 141 | 135 | 138 |
| | After thermal cycling (MPa) | 129 | 135 | 126 | 127 | 122 | 130 |

TABLE 1A-continued

Property test results of dental curable compositions

| | | | | | | |
|---|---|---|---|---|---|---|
| Maintenance rate of bending strengths (%) | 91.0 | 91.8 | 90.8 | 90.1 | 90.4 | 94.2 |

TABLE 1B

Property test results of dental curable compositions

| | | Comparative Example 1 | Comparative Example 2 | Comparative Example 3 | Comparative Example 4 | Comparative Example 5 | Comparative Example 6 |
|---|---|---|---|---|---|---|---|
| Binder resins | | A-1 | A-1 | A-1 | A-1 | A-1 | A-1 |
| Inorganic fillers (B) | Names | classified dry product (1) | B-12 | B-13 | B-14 | Silica Micro Bead P-500 | FUSELEX X |
| | Shapes | spherical porous | spherical non-porous | spherical porous | spherical porous | spherical porous | amorphous non-porous |
| | Compositions | $SiO_2/ZrO_2$ | $SiO_2/ZrO_2$ | $SiO_2/ZrO_2$ | $SiO_2/ZrO_2$ | Si/— | Si/— |
| | Combinations ratios (mass %) | 82/18 | 82/18 | 65/35 | 99.5/0.5 | 100/0 | 100/0 |
| | $I_1$ | 0.44 | 0.07 | 3.04 | 2.23 | 1.50 | 0.03 |
| | $I_2$ | 1.47 | 0.02 | 1.31 | 1.22 | 1.22 | 0.11 |
| | $I_1/I_2$ | 0.30 | 3.50 | 2.32 | 1.83 | 1.23 | 0.27 |
| Contrast ratios | | 0.19 | 0.19 | 0.51 | 0.52 | 0.56 | 0.68 |
| Bending strength | Initial (MPa) | 128 | 113 | 153 | 154 | 121 | 125 |
| | After thermal cycling (MPa) | 112 | 96 | 141 | 139 | 110 | 111 |
| | Maintenance rate of bending strength (%) | 87.5 | 85.0 | 92.2 | 90.4 | 91.2 | 88.8 |

Examples 1 to 12

It was recognized that for the inorganic fillers (B) in the dental curable compositions of Examples 1 to 12, the ratios ($I_1/I_2$) of a maximum absorbance ($I_1$) at 3730 to 3750 cm$^{-1}$ to a maximum absorbance ($I_2$) at 3000 to 3600 cm$^{-1}$ in the infrared absorption spectrum, are not less than 1 and not more than 3.

The dental curable compositions of Examples 1-12 were recognized to exhibit excellent contrast ratios, and have a contrast ratios capable of reproducing the color tone of natural teeth. Furthermore, since the mechanical strengths of the dental curable compositions of Examples 1 to 12 are high values for bending strengths at the initial and after the thermal cycling, the dental curable compositions were recognized to have excellent mechanical strengths and the durability on aged deterioration.

Comparative Example 1

Although the dental curable composition of the Comparative Example 1 has a contrast ratio capable of reproducing the color tone of natural teeth, the above-mentioned ratio $I_1/I_2$ of the inorganic filler (B) was no more than 1. Therefore, it was recognized that its bending strength after the thermal cycling was low and its durability on aged deterioration was poor although its initial bending strength was high.

Comparative Example 2

Although the dental curable composition of the Comparative Example 2 has a contrast ratio capable of reproducing the color tone of natural teeth, the shape of the inorganic filler (B) is non-porous and thereby its initial bending strength was recognized to be low. Furthermore, since the above-mentioned ratio of the inorganic filler (B) was not less than 3, its durability on aged deterioration was also recognized to be poor.

Comparative Examples 3 to 5

Since the $I_1/I_2$ of inorganic fillers (B) for the dental curable compositions of Comparative Examples 3-5 were not less than 1 and not more than 3, the durabilities on aged deterioration were excellent. However, their contrast ratios were high and the dental curable compositions were opaque, and thereby it was recognized to be difficult to reproduce the color tone of natural teeth.

Comparative Example 6

The dental curable composition of Comparative Example 6 had a high contrast ratio and was opaque, and thereby it was recognized to be difficult to reproduce the color tone of natural teeth. Moreover, since the above-mentioned ratios $I_1/I_2$ of the inorganic filler (B) was not more than 1, it was recognized that the bending strength at the initial and after the thermal cycling were low, and its durability on aged deterioration was also recognized to be poor.

The invention claimed is:
1. A dental curable composition comprising a curable resin (A), a porous inorganic filler (B), and a polymerization initiator (C),
wherein the porous inorganic filler (B) comprises a silicon dioxide and an oxide comprising at least one kind of the other metallic elements, and a ratio ($I_1/I_2$) of a maximum absorbance ($I_1$) of 3730 to 3750 cm$^{-1}$ to a maximum absorbance ($I_2$) of 3000 to 3600 cm$^{-1}$ in infrared absorption spectrum of the porous inorganic filler (B), is not less than 1 and not more than 3.

2. The dental curable composition according to claim 1 wherein the at least one kind of the other metallic elements of said porous inorganic filler (B) are oxides containing at least zirconium element.

* * * * *